(12) United States Patent
Liu et al.

(10) Patent No.: US 8,704,030 B2
(45) Date of Patent: *Apr. 22, 2014

(54) PROCESS OF SEPARATING GASES USING POLYIMIDE MEMBRANES

(75) Inventors: Chunqing Liu, Schaumburg, IL (US); Travis C. Bowen, Crystal Lake, IL (US); Emily G. Harbert, Chicago, IL (US); Raisa Minkov, Skokie, IL (US); Syed A. Faheem, Huntley, IL (US); Zara Osman, Niles, IL (US)

(73) Assignee: UOP LLC, Des Plaines, IL (US)

( * ) Notice: Subject to any disclaimer, the term of this patent is extended or adjusted under 35 U.S.C. 154(b) by 63 days.

This patent is subject to a terminal disclaimer.

(21) Appl. No.: 13/278,467

(22) Filed: Oct. 21, 2011

(65) Prior Publication Data

US 2012/0323059 A1  Dec. 20, 2012

Related U.S. Application Data

(60) Provisional application No. 61/498,116, filed on Jun. 17, 2011.

(51) Int. Cl.
*C07C 7/144* (2006.01)

(52) U.S. Cl.
USPC ........................................... 585/818

(58) Field of Classification Search
None
See application file for complete search history.

(56) References Cited

U.S. PATENT DOCUMENTS

| | | |
|---|---|---|
| 2004/0159233 A1* | 8/2004 | Simmons et al. ................. 95/45 |
| 2004/0177753 A1 | 9/2004 | Chung et al. |
| 2008/0143014 A1 | 6/2008 | Tang |
| 2012/0322119 A1 | 12/2012 | Liu et al. |
| 2012/0322646 A1 | 12/2012 | Liu et al. |
| 2012/0322911 A1 | 12/2012 | Liu et al. |

OTHER PUBLICATIONS

Grubb, "Highly soluble polyimides from sterically hindered diamines", Polymer 40 (1999) 4279-4288.

Park, "Relationship between chemical structure of aromatic polyimides and gas permeation properties of their carbon molecular sieve membranes", Journal of Membrane Science 229 (2004) 117-127.

* cited by examiner

*Primary Examiner* — Tam M Nguyen
(74) *Attorney, Agent, or Firm* — Mark Goldberg

(57) ABSTRACT

The present invention discloses a new type of polyimide membrane with high permeances and high selectivities for gas separations and particularly for $CO_2/CH_4$ and $H_2/CH_4$ separations. The polyimide membranes have $CO_2$ permeability of 50 Barrers or higher and single-gas selectivity for $CO_2/CH_4$ of 15 or higher at 50° C. under 791 kPa for $CO_2/CH_4$ separation. The polyimide membranes have UV cross-linkable functional groups and can be used for the preparation of UV cross-linked polyimide membranes having $CO_2$ permeability of 20 Barrers or higher and single-gas selectivity for $CO_2/CH_4$ of 35 or higher at 50° C. under 791 kPa for $CO_2/CH_4$ separation.

6 Claims, No Drawings

PROCESS OF SEPARATING GASES USING POLYIMIDE MEMBRANES

CROSS-REFERENCE TO RELATED APPLICATION

This application claims priority from Provisional Application No. 61/498,116 filed Jun. 17, 2011, the contents of which are hereby incorporated by reference.

BACKGROUND OF THE INVENTION

This invention relates to a new type of polyimide membrane with high permeances and high selectivities for gas separations and more particularly for use in natural gas upgrading and hydrogen purification.

In the past 30-35 years, the state of the art of polymer membrane-based gas separation processes has evolved rapidly. Membrane-based technologies are a low capital cost solution and provide high energy efficiency compared to conventional separation methods. Membrane gas separation is of special interest to petroleum producers and refiners, chemical companies, and industrial gas suppliers. Several applications of membrane gas separation have achieved commercial success, including $N_2$ enrichment from air, carbon dioxide removal from natural gas and from enhanced oil recovery, and also in hydrogen removal from nitrogen, methane, and argon in ammonia purge gas streams. For example, UOP's Separex™ cellulose acetate spiral wound polymeric membrane is currently an international market leader for carbon dioxide removal from natural gas.

Polymers provide a range of properties including low cost, permeability, mechanical stability, and ease of processability that are important for gas separation. Glassy polymers (i.e., polymers at temperatures below their $T_g$) have stiffer polymer backbones and therefore allow smaller molecules such as hydrogen and helium pass through more quickly, while larger molecules such as hydrocarbons pass through more slowly as compared to polymers with less stiff backbones. Cellulose acetate (CA) glassy polymer membranes are used extensively in gas separation. Currently, such CA membranes are used for natural gas upgrading, including the removal of carbon dioxide. Although CA membranes have many advantages, they are limited in a number of properties including selectivity, permeability, and in chemical, thermal, and mechanical stability. High performance polymers such as polyimides (PIs), poly(trimethylsilylpropyne), and polytriazole have been developed to improve membrane selectivity, permeability, and thermal stability. These polymeric membrane materials have shown promising intrinsic properties for separation of gas pairs such as $CO_2/CH_4$, $O_2/N_2$, $H_2/CH_4$, and propylene/propane ($C_3H_6/C_3H_8$).

The membranes most commonly used in commercial gas and liquid separation applications are asymmetric polymeric membranes and have a thin nonporous selective skin layer that performs the separation. Separation is based on a solution-diffusion mechanism. This mechanism involves molecular-scale interactions of the permeating gas with the membrane polymer. The mechanism assumes that in a membrane having two opposing surfaces, each component is sorbed by the membrane at one surface, transported by a gas concentration gradient, and desorbed at the opposing surface. According to this solution-diffusion model, the membrane performance in separating a given pair of gases (e.g., $CO_2/CH_4$, $O_2/N_2$, $H_2/CH_4$) is determined by two parameters: the permeability coefficient (abbreviated hereinafter as permeability or $P_A$) and the selectivity ($\alpha_{A/B}$). The $P_A$ is the product of the gas flux and the selective skin layer thickness of the membrane, divided by the pressure difference across the membrane. The $\alpha_{A/B}$ is the ratio of the permeability coefficients of the two gases ($\alpha_{A/B}=P_A/P_B$) where $P_A$ is the permeability of the more permeable gas and $P_B$ is the permeability of the less permeable gas. Gases can have high permeability coefficients because of a high solubility coefficient, a high diffusion coefficient, or because both coefficients are high. In general, the diffusion coefficient decreases while the solubility coefficient increases with an increase in the molecular size of the gas. In high performance polymer membranes, both high permeability and selectivity are desirable because higher permeability decreases the size of the membrane area required to treat a given volume of gas, thereby decreasing capital cost of membrane units, and because higher selectivity results in a higher purity product gas.

One of the components to be separated by a membrane must have a sufficiently high permeance at the preferred conditions or an extraordinarily large membrane surface area is required to allow separation of large amounts of material. Permeance, measured in Gas Permeation Units (GPU, 1 GPU=$10^{-6}$ cm$^3$ (STP)/cm$^2$ s (cm Hg)), is the pressure normalized flux and equals to permeability divided by the skin layer thickness of the membrane. Commercially available gas separation polymer membranes, such as CA, polyimide, and polysulfone membranes formed by phase inversion and solvent exchange methods have an asymmetric integrally skinned membrane structure. Such membranes are characterized by a thin, dense, selectively semipermeable surface "skin" and a less dense void-containing (or porous), nonselective support region, with pore sizes ranging from large in the support region to very small proximate to the "skin". However, it is very complicated and tedious to make such asymmetric integrally skinned membranes having a defect-free skin layer. The presence of nanopores or defects in the skin layer reduces the membrane selectivity. Another type of commercially available gas separation polymer membrane is the thin film composite (or TFC) membrane, comprising a thin selective skin deposited on a porous support. TFC membranes can be formed from CA, polysulfone, polyethersulfone, polyamide, polyimide, polyetherimide, cellulose nitrate, polyurethane, polycarbonate, polystyrene, etc. Fabrication of TFC membranes that are defect-free is also difficult, and requires multiple steps. Yet another approach to reduce or eliminate the nanopores or defects in the skin layer of the asymmetric membranes has been the fabrication of an asymmetric membrane comprising a relatively porous and substantial void-containing selective "parent" membrane such as polysulfone or cellulose acetate that would have high selectivity were it not porous, in which the parent membrane is coated with a material such as a polysiloxane, a silicone rubber, or a UV-curable epoxysilicone in occluding contact with the porous parent membrane, the coating filling surface pores and other imperfections comprising voids. The coating of such coated membranes, however, is subject to swelling by solvents, poor performance durability, low resistance to hydrocarbon contaminants, and low resistance to plasticization by the sorbed penetrant molecules such as $CO_2$ or $C_3H_6$.

Many of the deficiencies of these prior art membranes are improved in the present invention which provides a new type of polyimide membrane with high permeances and high selectivities for gas separations.

SUMMARY OF THE INVENTION

A new type of polyimide membrane with high permeances and high selectivities for gas separations has been made.

The present invention generally relates to gas separation membranes and, more particularly, to high permeance and high selectivity polyimide membranes for gas separations. The polyimide membranes with high permeances and high selectivities described in the current invention have $CO_2$ permeability at least 50 Barrer (1 Barrer=$10^{-10}$ cm$^3$ (STP) cm/cm$^2$ s (cm Hg)) and single-gas $CO_2/CH_4$ selectivity at least 15 at 50° C. under 791 kPa feed pressure.

The present invention provides a new type of polyimide membranes with high permeance and high selectivity for gas separations. One polyimide membrane described in the present invention is fabricated from poly(3,3',4,4'-diphenylsulfone tetracarboxylic dianhydride-2,4,6-trimethyl-m-phenylenediamine) polyimide (abbreviated as NPI-1), which is derived from the polycondensation reaction of 3,3',4,4'-diphenylsulfone tetracarboxylic dianhydride (DSDA) with 2,4,6-trimethyl-m-phenylenediamine (TMPDA). Tests showed that this NPI-1 polyimide membrane has an intrinsic $CO_2$ permeability of 73.4 Barrers and single-gas $CO_2/CH_4$ selectivity of 25.3 at 50° C. under 791 kPa for $CO_2/CH_4$ separation. This membrane also has intrinsic $H_2$ permeability of 136.6 Barrers and single-gas $H_2/CH_4$ selectivity of 47.1 at 50° C. under 791 kPa for $H_2/CH_4$ separation. This NPI-1 polyimide membrane contains UV cross-linkable sulfonic groups.

Another polyimide membrane described in the present invention is fabricated from poly(3,3',4,4'-diphenylsulfone tetracarboxylic dianhydride-3,3',4,4'-biphenyl tetracarboxylic dianhydride-2,4,6-trimethyl-m-phenylenediamine-3,3',5,5'-tetramethyl-4,4'-methylene dianiline) polyimide (abbreviated as NPI-2), which is derived from the polycondensation reaction of DSDA and 3,3',4,4'-biphenyl tetracarboxylic dianhydride (BPDA) with 3,3',5,5'-tetramethyl-4,4'-methylene dianiline (TMMDA) and TMPDA (DSDA:BPDA:TMMDA:TMPDA=3.06:1.02:2.00:2.00 (molar ratio)). Pure gas permeation results showed that this NPI-2 membrane has an intrinsic $CO_2$ permeability of 57.5 Barrers and single-gas $CO_2/CH_4$ selectivity of 20.2 at 50° C. under 791 kPa for $CO_2/CH_4$ separation. This membrane also has intrinsic $H_2$ permeability of 109.9 Barrers and single-gas $H_2/CH_4$ selectivity of 38.6 at 50° C. under 791 kPa for $H_2/CH_4$ separation. This NPI-2 membrane contains UV cross-linkable sulfonic groups.

Yet another polyimide membrane that is a part of the present invention is fabricated from poly(3,3',4,4'-benzophenone tetracarboxylic dianhydride-pyromellitic dianhydride-2,4,6-trimethyl-m-phenylenediamine) polyimide (abbreviated as NPI-3), which is derived from the polycondensation reaction of 3,3',4,4'-benzophenone tetracarboxylic dianhydride (BTDA) and pyromellitic dianhydride (PMDA) with TMPDA (BTDA:PMDA:TMPDA=2.04:2.04:4.00 (molar ratio)). Pure gas permeation results showed that this NPI-3 membrane has an intrinsic $CO_2$ permeability of 179 Barrers and single-gas $CO_2/CH_4$ selectivity of 15.8 at 50° C. under 791 kPa for $CO_2/CH_4$ separation. This membrane also has intrinsic $H_2$ permeability of 256.5 Barrers and single-gas $H_2/CH_4$ selectivity of 22.7 at 50° C. under 791 kPa for $H_2/CH_4$ separation. This NPI-3 membrane contains UV cross-linkable carbonyl groups.

Yet another polyimide membrane that is a part of the present invention is fabricated from poly(3,3',4,4'-benzophenone tetracarboxylic dianhydride-pyromellitic dianhydride-2,4,6-trimethyl-m-phenylenediamine-3,3',5,5'-tetramethyl-4,4'-methylene dianiline) polyimide (abbreviated as NPI-4), which is derived from the polycondensation reaction of BTDA and PMDA with TMPDA and TMMDA (BTDA:PMDA:TMPDA:TMMDA=2.04:2.04:2.00:2.00 (molar ratio)). Pure gas permeation results showed that this NPI-4 membrane has an intrinsic $CO_2$ permeability of 97.0 Barrers and single-gas $CO_2/CH_4$ selectivity of 17.1 at 50° C. under 791 kPa for $CO_2/CH_4$ separation. This membrane also has intrinsic $H_2$ permeability of 159.5 Barrers and single-gas $H_2/CH_4$ selectivity of 28.2 at 50° C. under 791 kPa for $H_2/CH_4$ separation. This NPI-4 membrane contains UV cross-linkable carbonyl groups.

In another embodiment of the invention, this invention pertains to high performance polyimide membranes that have undergone an additional crosslinking step, by chemical or UV crosslinking or other crosslinking process as known to one skilled in the art. A cross-linked polyimide membrane can be prepared by UV cross-linking of the polyimide membrane via exposure of the membrane to UV radiation. The polyimide polymers used for the preparation of the polyimide membranes described in the current invention have UV cross-linkable sulfonic (—$SO_2$—) or carbonyl (—C(O)—) functional groups. The cross-linked polyimide membranes comprise polymer chain segments where at least part of these polymer chain segments are cross-linked to each other through possible direct covalent bonds by exposure to UV radiation. The cross-linking of the polyimide membranes provides the membranes with improved selectivities and decreased permeances compared to the corresponding uncross-linked polyimide membranes.

The membrane dope formulation for the preparation of polyimide membranes with high permeances for gas separations in the present invention comprises N-methylpyrrolidone (NMP) and 1,3-dioxolane which are good solvents for the polyimide polymer. In some cases, the membrane dope formulation for the preparation of polyimide membranes with high permeances and high selectivities for gas separations in the present invention also comprises acetone and isopropanol (or methanol) which are poor solvents for the polyimide polymer. The new polyimide membranes with high permeances and high selectivities for gas separations described in the current invention have either flat sheet (spiral wound) or hollow fiber geometry. In some cases, the selective skin layer surface of the polyimide membranes is coated with a thin layer of material such as a polysiloxane, a fluoropolymer, a thermally curable silicone rubber, or a UV radiation cured silicone rubber.

The invention provides a process for separating at least one gas from a mixture of gases using the new polyimide membranes with high permeances and high selectivities described herein, the process comprising: (a) providing a polyimide membrane with high permeance and high selectivity described in the present invention which is permeable to said at least one gas; (b) contacting the mixture on one side of the polyimide membrane to cause said at least one gas to permeate the membrane; and (c) removing from the opposite side of the membrane a permeate gas composition comprising a portion of said at least one gas which permeated said membrane.

The new polyimide membranes with high permeances and high selectivities are not only suitable for a variety of liquid, gas, and vapor separations such as desalination of water by reverse osmosis, non-aqueous liquid separation such as deep desulfurization of gasoline and diesel fuels, ethanol/water separations, pervaporation dehydration of aqueous/organic mixtures, $CO_2/CH_4$, $CO_2/N_2$, $H_2/CH_4$, $O_2/N_2$, $H_2S/CH_4$, olefin/paraffin, iso/normal paraffins separations, and other light gas mixture separations, but also can be used for other applications such as for catalysis and fuel cell applications.

DETAILED DESCRIPTION OF THE INVENTION

The use of membranes for separation of both gases and liquids is a growing technological area with potentially high economic reward due to the low energy requirements and the potential for scaling up of modular membrane designs. Advances in membrane technology, with the continuing development of new membrane materials and new methods for the production of high performance membranes will make this technology even more competitive with traditional, high-energy intensive and costly processes such as distillation. Among the applications for large scale gas separation membrane systems are nitrogen enrichment, oxygen enrichment, hydrogen recovery, removal of hydrogen sulfide and carbon dioxide from natural gas and dehydration of air and natural gas. Various hydrocarbon separations are potential applications for the appropriate membrane system. The membranes that are used in these applications must have high selectivity, durability, and productivity in processing large volumes of gas or liquid in order to be economically successful. Membranes for gas separations have evolved rapidly in the past 25 years due to their easy processability for scale-up and low energy requirements. More than 90% of the membrane gas separation applications involve the separation of noncondensable gases such as carbon dioxide from methane, nitrogen from air, and hydrogen from nitrogen, argon or methane. Membrane gas separation is of special interest to petroleum producers and refiners, chemical companies, and industrial gas suppliers. Several applications of membrane gas separation have achieved commercial success, including nitrogen enrichment from air, carbon dioxide removal from natural gas and biogas and in enhanced oil recovery.

The present invention provides a new type of polyimide membranes with high permeances and high selectivities for gas separations. This invention also pertains to the application of these polyimide membranes with high permeances and high selectivities for a variety of gas separations such as separations of $CO_2/CH_4$, $H_2S/CH_4$, $CO_2/N_2$, olefin/paraffin separations (e.g. propylene/propane separation), $H_2/CH_4$, $O_2/N_2$, iso/normal paraffins, polar molecules such as $H_2O$, $H_2S$, and $NH_3$/mixtures with $CH_4$, $N_2$, $H_2$, and other light gases separations, as well as for liquid separations such as desalination and pervaporation.

The membrane dope formulation for the preparation of polyimide membranes with high permeances and high selectivities for gas separations in the present invention comprises good solvents for the polyimide polymer that can completely dissolve the polymer. Representative good solvents for use in this invention include N-methylpyrrolidone (NMP), N,N-dimethyl acetamide (DMAC), methylene chloride, N,N-dimethylformamide (DMF), dimethyl sulfoxide (DMSO), dioxanes, 1,3-dioxolane, mixtures thereof, others known to those skilled in the art and mixtures thereof. In some cases, the membrane dope formulation for the preparation of polyimide membranes with high permeances and high selectivities for gas separations in the present invention also comprises poor solvents for the polyimide polymer that cannot dissolve the polymer such as acetone, methanol, ethanol, tetrahydrofuran (THF), toluene, n-octane, n-decane, lactic acid, citric acid, isopropanol, and mixtures thereof. It is believed that the proper weight ratio of the solvents used in the present invention provides asymmetric polyimide membranes with <100 nm super thin nonporous selective skin layer which results in high permeances. The polyimide membranes with high permeances and high selectivities described in the present invention have $CO_2$ permeability of at least 50 Barrers and single-gas $CO_2/CH_4$ selectivity at least 15 at 50° C. under 791 kPa feed pressure.

The present invention provides a new type of polyimide membranes with high permeances and high selectivities for gas separations. One polyimide membrane described in the present invention is fabricated from poly(3,3',4,4'-diphenylsulfone tetracarboxylic dianhydride-2,4,6-trimethyl-m-phenylenediamine) polyimide (abbreviated as NPI-1), which is derived from the polycondensation reaction of 3,3',4,4'-diphenylsulfone tetracarboxylic dianhydride (DSDA) with 2,4,6-trimethyl-m-phenylenediamine (TMPDA). Tests showed that this NPI-1 polyimide membrane has an intrinsic $CO_2$ permeability of 73.4 Barrers and single-gas $CO_2/CH_4$ selectivity of 25.3 at 50° C. under 791 kPa for $CO_2/CH_4$ separation. This membrane also has intrinsic $H_2$ permeability of 136.6 Barrers and single-gas $H_2/CH_4$ selectivity of 47.1 at 50° C. under 791 kPa for $H_2/CH_4$ separation. This NPI-1 polyimide membrane contains UV cross-linkable sulfonic groups.

Another polyimide membrane described in the present invention is fabricated from poly(3,3',4,4'-diphenylsulfone tetracarboxylic dianhydride-3,3',4,4'-biphenyl tetracarboxylic dianhydride-2,4,6-trimethyl-m-phenylenediamine-3,3',5,5'-tetramethyl-4,4'-methylene dianiline) polyimide (abbreviated as NPI-2), which is derived from the polycondensation reaction of DSDA and 3,3',4,4'-biphenyl tetracarboxylic dianhydride (BPDA) with 3,3',5,5'-tetramethyl-4,4'-methylene dianiline (TMMDA) and TMPDA (DSDA:BPDA:TMMDA:TMPDA=3.06:1.02:2.00:2.00 (molar ratio)). Pure gas permeation results showed that this NPI-2 membrane has an intrinsic $CO_2$ permeability of 57.5 Barrers and single-gas $CO_2/CH_4$ selectivity of 20.2 at 50° C. under 791 kPa for $CO_2/CH_4$ separation. This membrane also has intrinsic $H_2$ permeability of 109.9 Barrers and single-gas $H_2/CH_4$ selectivity of 38.6 at 50° C. under 791 kPa for $H_2/CH_4$ separation. This NPI-2 membrane contains UV cross-linkable sulfonic groups.

Yet another polyimide membrane that is a part of the present invention is fabricated from poly(3,3',4,4'-benzophenone tetracarboxylic dianhydride-pyromellitic dianhydride-2,4,6-trimethyl-m-phenylenediamine) polyimide (abbreviated as NPI-3), which is derived from the polycondensation reaction of 3,3',4,4'-benzophenone tetracarboxylic dianhydride (BTDA) and pyromellitic dianhydride (PMDA) with TMPDA (BTDA:PMDA:TMPDA=2.04:2.04:4.00 (molar ratio)). Pure gas permeation results showed that this NPI-3 membrane has an intrinsic $CO_2$ permeability of 179 Barrers and single-gas $CO_2/CH_4$ selectivity of 15.8 at 50° C. under 791 kPa for $CO_2/CH_4$ separation. This membrane also has intrinsic $H_2$ permeability of 256.5 Barrers and single-gas $H_2/CH_4$ selectivity of 22.7 at 50° C. under 791 kPa for $H_2/CH_4$ separation. This NPI-3 membrane contains UV cross-linkable carbonyl groups.

Yet another polyimide membrane that is a part of the present invention is fabricated from poly(3,3',4,4'-benzophenone tetracarboxylic dianhydride-pyromellitic dianhydride-2,4,6-trimethyl-m-phenylenediamine-3,3',5,5'-tetramethyl-4,4'-methylene dianiline) polyimide (abbreviated as NPI-4), which is derived from the polycondensation reaction of BTDA and PMDA with TMPDA and TMMDA (BTDA:PMDA:TMPDA:TMMDA=2.04:2.04:2.00:2.00 (molar ratio)). Pure gas permeation results showed that this NPI-4 membrane has an intrinsic $CO_2$ permeability of 97.0 Barrers and single-gas $CO_2/CH_4$ selectivity of 17.1 at 50° C. under 791 kPa for $CO_2/CH_4$ separation. This membrane also has intrinsic $H_2$ permeability of 159.5 Barrers and single-gas $H_2/CH_4$ selectivity of 28.2 at 50° C. under 791 kPa for $H_2/CH_4$ separation. This NPI-4 membrane contains UV cross-linkable carbonyl groups.

In some cases, the high performance polyimide membranes described in the present invention have undergone an additional crosslinking step, by chemical or UV crosslinking or other crosslinking process as known to one skilled in the art. A cross-linked polyimide membrane can be prepared by UV cross-linking of the polyimide membrane via exposure of the membrane to UV radiation. The polyimide polymers used for the preparation of the polyimide membranes described in the current invention have UV cross-linkable sulfonic (—$SO_2$—) or carbonyl (—C(O)—) functional groups. The cross-linked polyimide membranes comprise polymer chain segments where at least part of these polymer chain segments are cross-linked to each other through possible direct covalent bonds by exposure to UV radiation. The cross-linking of the polyimide membranes provides the membranes with improved selectivities and decreased permeances compared to the corresponding uncross-linked polyimide membranes. The UV cross-linked polyimide membranes described in the current invention have $CO_2$ permeability of 20 Barrers or higher and single-gas selectivity for $CO_2/CH_4$ of 35 or higher at 50° C. under 791 kPa for $CO_2/CH_4$ separation.

Optimization of the cross-linking degree in the UV cross-linked polyimide membrane described in the present invention should promote the tailoring of membranes for a wide range of gas and liquid separations with improved permeation properties and environmental stability. The cross-linking degree of the UV-cross-linked polyimide membranes of the present invention can be controlled by adjusting the distance between the UV lamp and the membrane surface, UV radiation time, wavelength and strength of UV light, etc. Preferably, the distance from the UV lamp to the membrane surface is in the range of 0.8 to 25.4 cm (0.3 to 10 inches) with a UV light provided from 12 watt to 450 watt low pressure or medium pressure mercury arc lamp, and the UV radiation time is in the range of 0.5 min to 1 h. More preferably, the distance from the UV lamp to the membrane surface is in the range of 1.3 to 5.1 cm (0.5 to 2 inches) with a UV light provided from 12 watt to 450 watt low pressure or medium pressure mercury arc lamp, and the UV radiation time is in the range of 1 to 40 minutes.

As an example, UV cross-linked NPI-4 membrane is prepared by further UV cross-linking the UV cross-linkable NPI-4 membrane using a UV lamp from a certain distance and for a period of time selected based upon the separation properties sought. For example, UV cross-linked NPI-4 membrane can be prepared from NPI-4 membrane by exposure to UV radiation using 254 nm wavelength UV light generated from a UV lamp with 1.9 cm (0.75 inch) distance from the membrane surface to the UV lamp and a radiation time of 10 min at 50° C. The UV lamp described here is a low pressure, mercury arc immersion UV quartz 12 watt lamp with 12 watt power supply from Ace Glass Incorporated. Pure gas permeation results showed that the UV cross-linked NPI-4 membrane has an intrinsic $CO_2$ permeability of 39.3 Barrers and single-gas $CO_2/CH_4$ selectivity of 41.2 at 50° C. under 791 kPa for $CO_2/CH_4$ separation. This UV cross-linked NPI-4 membrane also has intrinsic $H_2$ permeability of 149.8 Barrers and single-gas $H_2/CH_4$ selectivity of 156.8 at 50° C. under 791 kPa for $H_2/CH_4$ separation. These results indicate that the UV cross-linked NPI-4 membrane has significantly enhanced single-gas $CO_2/CH_4$ selectivity and single-gas $H_2/CH_4$ selectivity compared to the uncross-linked NPI-4 membrane.

The polyimide polymers used for making the polyimide membranes with high permeances and high selectivities described in the current invention may comprise a plurality of first repeating units of formula (I):

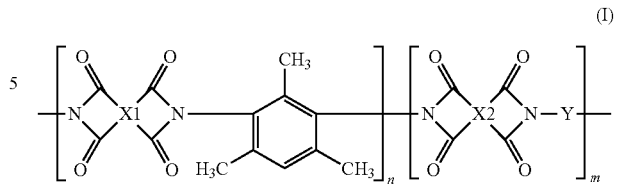

wherein X1 is selected from the group consisting of

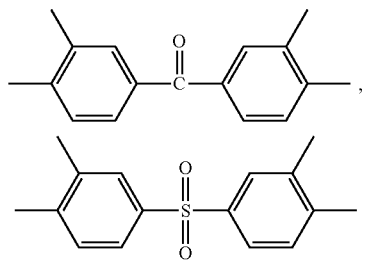

and mixtures thereof. X2 is selected from the group consisting of

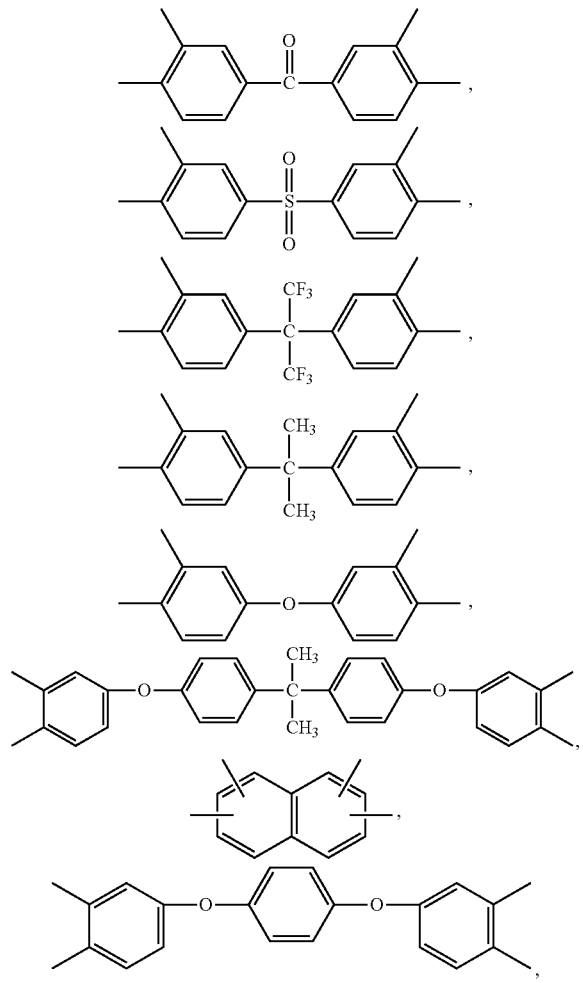

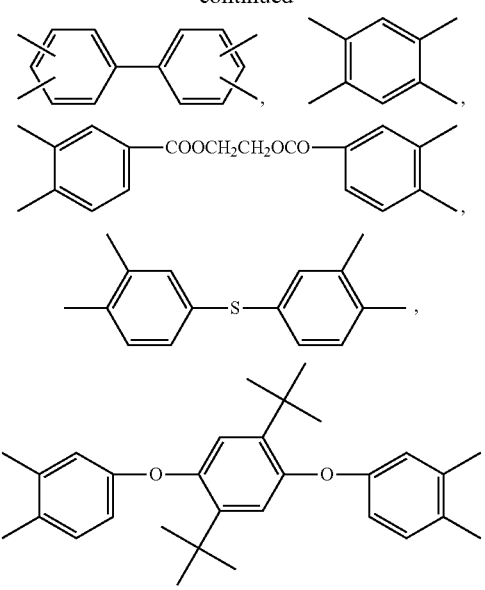

and mixtures thereof. Y is selected from the group consisting of

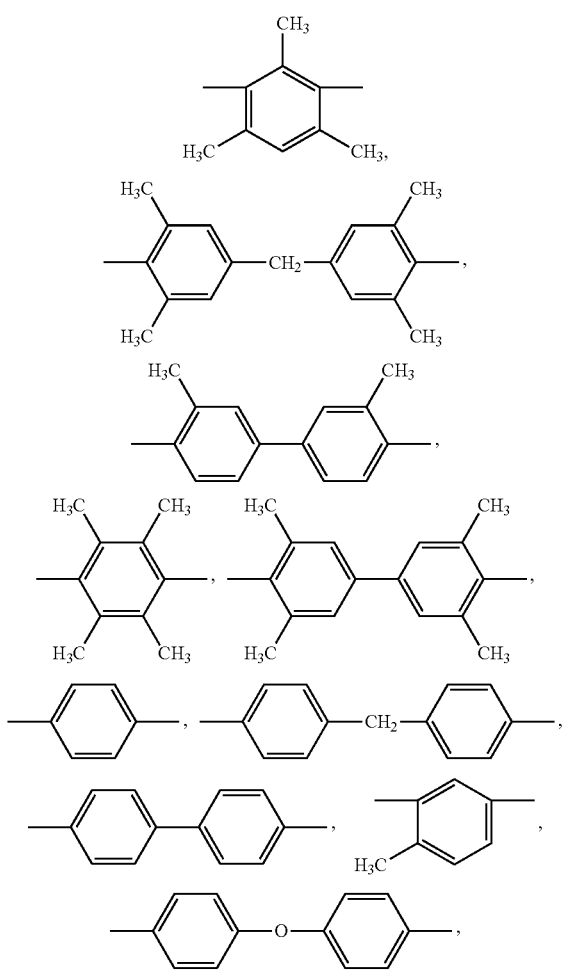

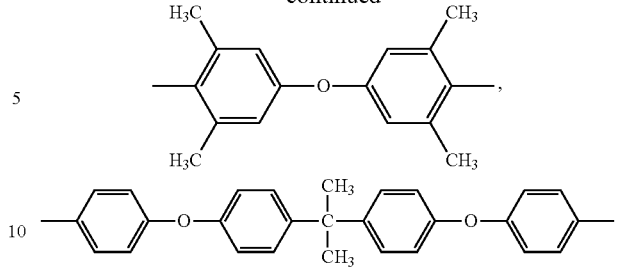

and mixtures thereof and n and m are independent integers from 2 to 500.

The polyimide polymers used for making the polyimide membranes with high permeances and high selectivities described in the current invention have a weight average molecular weight in the range of 50,000 to 1,000,000 Daltons, preferably between 70,000 to 500,000 Daltons.

Some examples of polyimide polymers used for making the polyimide membranes with high permeances and high selectivities described in the current invention may include, but are not limited to: poly(3,3',4,4'-diphenylsulfone tetracarboxylic dianhydride-2,4,6-trimethyl-m-phenylenediamine) polyimide (abbreviated as NPI-1) derived from the polycondensation reaction of 3,3',4,4'-diphenylsulfone tetracarboxylic dianhydride (DSDA) with 2,4,6-trimethyl-m-phenylenediamine (TMPDA); poly(3,3',4,4'-diphenylsulfone tetracarboxylic dianhydride-3,3',4,4'-biphenyl tetracarboxylic dianhydride-2,4,6-trimethyl-m-phenylenediamine-3,3',5,5'-tetramethyl-4,4'-methylene dianiline) polyimides derived from the polycondensation reaction of DSDA and 3,3',4,4'-biphenyl tetracarboxylic dianhydride (BPDA) with 3,3',5,5'-tetramethyl-4,4'-methylene dianiline (TMMDA) and TMPDA (abbreviated as NPI-2 when DSDA:BPDA:TMMDA:TMPDA=3.06:1.02:2.00:2.00 (molar ratio) and abbreviated as NPI-5 when DSDA:BPDA:TMMDA:TMPDA=2.04:2.04:1.00:3.00 (molar ratio)); poly(3,3',4,4'-benzophenone tetracarboxylic dianhydride-pyromellitic dianhydride-2,4,6-trimethyl-m-phenylenediamine) polyimides derived from the polycondensation reaction of 3,3',4,4'-benzophenone tetracarboxylic dianhydride (BTDA) and pyromellitic dianhydride (PMDA) with TMPDA (abbreviated as NPI-3 when BTDA:PMDA:TMPDA=2.04:2.04:4.00 (molar ratio) and abbreviated as NPI-6 when BTDA:PMDA:TMPDA=2.45:1.63:4.00 (molar ratio)); poly(3,3',4,4'-benzophenone tetracarboxylic dianhydride-pyromellitic dianhydride-2,4,6-trimethyl-m-phenylenediamine-3,3',5,5'-tetramethyl-4,4'-methylene dianiline) polyimide (abbreviated as NPI-4) derived from the polycondensation reaction of BTDA and PMDA with TMPDA and TMMDA (BTDA:PMDA:TMPDA:TMMDA=2.04:2.04:2.00:2.00 (molar ratio)).

The polyimide membranes described in the present invention can be fabricated into any convenient geometry such as flat sheet (or spiral wound), tube, or hollow fiber.

The present invention also involves blend polymer membranes comprising the polyimide polymers used for making the polyimide membranes with high permeances and high selectivities described in the current invention. In some embodiments of the invention, the blend polymer membranes comprising the polyimide polymers used for making the polyimide membranes with high permeances and high selectivities described in the current invention may be subjected to an additional crosslinking step to increase the selectivity of the membrane.

The term "blend polymer membrane" in the present invention refers to a membrane prepared from a blend of two or more polymers. The blend polymer membrane comprising the polyimide polymers used for making the polyimide membranes with high permeances and high selectivities described in the current invention contains a blend of two or more polymers wherein at least one polymer is a polyimide polymer described in the present invention.

In some cases, it is desirable to cross-link the blend polymer membrane to improve the membrane selectivity. The cross-linked blend polymer membrane described in the current invention is prepared by UV cross-linking of the blend polymer membrane comprising at least one polyimide polymer used for making the polyimide membranes with high permeances and high selectivities described in the current invention. After UV cross-linking, the cross-linked blend polymer membrane comprises polymer chain segments wherein at least part of these polymer chain segments are cross-linked to each other through possible direct covalent bonds by exposure to UV radiation. The cross-linking of the blend polymer membranes offers the membranes superior selectivity and improved chemical and thermal stabilities than the corresponding uncross-linked blend polymer membranes comprising at least one polyimide polymer used for making the polyimide membranes with high permeances and high selectivities described in the current invention.

The second polymer in the blend polymer membrane comprising the polyimide polymers described in the current invention can be selected from, but is not limited to, polysulfones; sulfonated polysulfones; polyethersulfones; sulfonated polyethersulfones; and polyvinylpyrrolidones. The invention provides a process for separating at least one gas from a mixture of gases using the new polyimide membranes with high permeances and high selectivities described in the present invention, the process comprising: (a) providing a polyimide membrane with high permeance and high selectivity described in the present invention which is permeable to the at least one gas; (b) contacting the mixture on one side of the asymmetric polyimide membrane with high permeance described in the present invention to cause the at least one gas to permeate the membrane; and (c) removing from the opposite side of the membrane a permeate gas composition comprising a portion of the at least one gas which permeated the asymmetric polyimide membrane.

The polyimide membranes with high permeances and high selectivities described in the present invention are especially useful in the purification, separation or adsorption of a particular species in the liquid or gas phase. In addition to separation of pairs of gases, these polyimide membranes with high permeances and high selectivities described in the present invention may, for example, be used for the desalination of water by reverse osmosis or for the separation of proteins or other thermally unstable compounds, e.g. in the pharmaceutical and biotechnology industries. The polyimide membranes with high permeances and high selectivities described in the present invention may also be used in fermenters and bioreactors to transport gases into the reaction vessel and transfer cell culture medium out of the vessel. Additionally, these polyimide membranes with high permeances and high selectivities described in the present invention may be used for the removal of microorganisms from air or water streams, water purification, and ethanol production in a continuous fermentation/membrane pervaporation system, and in detection or removal of trace compounds or metal salts in air or water streams.

The polyimide membranes with high permeances and high selectivities described in the present invention are especially useful in gas separation processes in air purification, petrochemical, refinery, and natural gas industries. Examples of such separations include separation of volatile organic compounds (such as toluene, xylene, and acetone) from an atmospheric gas, such as nitrogen or oxygen and nitrogen recovery from air. Further examples of such separations are for the separation of $CO_2$ or $H_2S$ from natural gas, $H_2$ from $N_2$, $CH_4$, and Ar in ammonia purge gas streams, $H_2$ recovery in refineries, olefin/paraffin separations such as propylene/propane separation, and iso/normal paraffin separations. Any given pair or group of gases that differ in molecular size, for example nitrogen and oxygen, carbon dioxide and methane, hydrogen and methane or carbon monoxide, helium and methane, can be separated using the polyimide membranes with high permeances described in the present invention. More than two gases can be removed from a third gas. For example, some of the gas components which can be selectively removed from a raw natural gas using the membrane described herein include carbon dioxide, oxygen, nitrogen, water vapor, hydrogen sulfide, helium, and other trace gases. Some of the gas components that can be selectively retained include hydrocarbon gases. When permeable components are acid components selected from the group consisting of carbon dioxide, hydrogen sulfide, and mixtures thereof and are removed from a hydrocarbon mixture such as natural gas, one module, or at least two in parallel service, or a series of modules may be utilized to remove the acid components. For example, when one module is utilized, the pressure of the feed gas may vary from 275 kPa to about 7.5 MPa (25 to 4000 psig). The differential pressure across the membrane can be as low as about 70 kPa or as high as 14.5 MPa (about 10 psi or as high as about 2100 psi) depending on many factors such as the particular membrane used, the flow rate of the inlet stream and the availability of a compressor to compress the permeate stream if such compression is desired. Differential pressure greater than about 14.5 MPa (2100 psi) may rupture the membrane. A differential pressure of at least 0.7 MPa (100 psi) is preferred since lower differential pressures may require more modules, more time and compression of intermediate product streams. The operating temperature of the process may vary depending upon the temperature of the feed stream and upon ambient temperature conditions. Preferably, the effective operating temperature of the membranes of the present invention will range from about −50° to about 150° C. More preferably, the effective operating temperature of the polyimide membranes with high permeances of the present invention will range from about −20° to about 100° C., and most preferably, the effective operating temperature of the membranes of the present invention will range from about 25° to about 100° C.

The polyimide membranes with high permeances and high selectivities described in the present invention are also especially useful in gas/vapor separation processes in chemical, petrochemical, pharmaceutical and allied industries for removing organic vapors from gas streams, e.g. in off-gas treatment for recovery of volatile organic compounds to meet clean air regulations, or within process streams in production plants so that valuable compounds (e.g., vinylchloride monomer, propylene) may be recovered. Further examples of gas/vapor separation processes in which polyimide membranes with high permeances and high selectivities and described in the present invention may be used are hydrocarbon vapor separation from hydrogen in oil and gas refineries, for hydrocarbon dew pointing of natural gas (i.e. to decrease the hydrocarbon dew point to below the lowest possible export pipeline temperature so that liquid hydrocarbons do not separate in the pipeline), for control of methane number in fuel gas for gas engines and gas turbines, and for gasoline recovery. The polyimide membranes with high permeances and high selectivities described in the present invention may incorporate a species that adsorbs strongly to certain gases (e.g. cobalt porphyrins or phthalocyanines for $O_2$ or silver (I) for ethane) to facilitate their transport across the membrane.

The polyimide membranes with high permeances and high selectivities described in the present invention also have immediate application to concentration of olefins in a paraffin/olefin stream for an olefin cracking application. For example, the polyimide membranes with high permeances and high selectivities described in the present invention can be used for propylene/propane separation to increase the concentration of the effluent in a catalytic dehydrogenation reaction for the production of propylene from propane and isobutylene from isobutane. Therefore, the number of stages of a propylene/propane splitter that is required to get polymer grade propylene can be reduced. Another application for the polyimide membranes with high permeances and high selectivities described in the present invention is for separating isoparaffin and normal paraffin in light paraffin isomerization and MaxEne™, a process for enhancing the concentration of normal paraffin (n-paraffin) in the naphtha cracker feedstock, which can be then converted to ethylene.

The polyimide membranes with high permeances and high selectivities described in the present invention can also be operated at high temperature to provide the sufficient dew point margin for natural gas upgrading (e.g, $CO_2$ removal from natural gas). The polyimide membranes with high permeances and high selectivities described in the present invention can be used in either a single stage membrane or as the first or/and second stage membrane in a two stage membrane system for natural gas upgrading. The polyimide membranes with high permeances and high selectivities described in the present invention have high selectivity, high permeance, high mechanical stability, and high thermal and chemical stabilities that allow the membranes to be operated without a costly pretreatment system. Due to the elimination of the pretreatment system and the significant reduction of membrane area, the new process can achieve significant capital cost saving and reduce the existing membrane footprint.

These polyimide membranes with high permeances and high selectivities described in the present invention may also be used in the separation of liquid mixtures by pervaporation, such as in the removal of organic compounds (e.g., alcohols, phenols, chlorinated hydrocarbons, pyridines, ketones) from water such as aqueous effluents or process fluids. A membrane which is ethanol-selective would be used to increase the ethanol concentration in relatively dilute ethanol solutions (5-10% ethanol) obtained by fermentation processes. Another liquid phase separation example using these polyimide membranes with high permeances and high selectivities described in the present invention is the deep desulfurization of gasoline and diesel fuels by a pervaporation membrane process similar to the process described in U.S. Pat. No. 7,048,846, incorporated by reference herein in its entirety. The polyimide membranes with high permeances and high selectivities described in the present invention that are selective to sulfur-containing molecules would be used to selectively remove sulfur-containing molecules from fluid catalytic cracking (FCC) and other naphtha hydrocarbon streams. Further liquid phase examples include the separation of one organic component from another organic component, e.g. to separate isomers of organic compounds. Mixtures of organic compounds which may be separated using polyimide membranes with high permeances described in the present invention include: ethylacetate-ethanol, diethylether-ethanol, acetic acid-ethanol, benzene-ethanol, chloroform-ethanol, chloroform-methanol, acetone-isopropylether, allylalcohol-allylether, allylalcohol-cyclohexane, butanol-butylacetate, butanol-1-butylether, ethanol-ethylbutylether, propylacetate-propanol, isopropylether-isopropanol, methanol-ethanol-isopropanol, and ethylacetate-ethanol-acetic acid.

EXAMPLES

The following examples are provided to illustrate one or more preferred embodiments of the invention, but are not limited embodiments thereof. Numerous variations can be made to the following examples that lie within the scope of the invention.

Example 1

Preparation of Polyimide Dense Film Membrane Using poly(3,3',4,4'-diphenylsulfone tetracarboxylic dianhydride-2,4,6-trimethyl-m-phenylenediamine) polyimide (NPI-1)

An aromatic poly(3,3',4,4'-diphenylsulfone tetracarboxylic dianhydride-2,4,6-trimethyl-m-phenylenediamine) polyimide (abbreviated as NPI-1) containing UV cross-linkable sulfonic groups was synthesized from 3,3',4,4'-diphenylsulfone tetracarboxylic dianhydride (DSDA) and 2,4,6-trimethyl-m-phenylenediamine (TMPDA) in DMAc polar solvent by a two-step process involving the formation of the poly(amic acid) followed by a solution imidization process. Acetic anhydride was used as the dehydrating agent and pyridine was used as the imidization catalyst for the solution imidization reaction. For example, a 250 mL three-neck round-bottom flask equipped with a nitrogen inlet and a mechanical stirrer was charged with 10.5 g of TMPDA and 42 g of DMAc. Once TMPDA was fully dissolved, 25.8 g of DSDA solid powder was added to the solution of TMPDA stepwise under stirring in the flask. 50 g of dimethylacetamide (DMAc) was added to the solution after the TMPDA powder was added. The reaction mixture was mechanically stirred for 24 hours at ambient temperature to give a viscous poly(amic acid) solution. Then 14.7 g of acetic anhydride was added slowly to the reaction mixture under stirring followed by the addition of 22.8 g of pyridine to the reaction mixture. The reaction mixture was mechanically stirred for an additional 2.0 hours at 90° C. to yield a polyimide designated as NPI-1 for the purpose of this application. The NPI-1 product in a fine fiber form was recovered by slowly precipitating the reaction mixture into a large amount of methanol and acetone mixture with 1:1 volume ratio. The resultant NPI-1 polyimide fibers were then thoroughly rinsed with methanol and dried in a vacuum oven at 100° C. for 24 hours.

The NPI-1 polymer dense film membrane was prepared as follows: 12.0 g of NPI-1 polyimide was dissolved in a solvent mixture of 19.5 g of NMP and 13.7 g of 1,3-dioxolane. The mixture was mechanically stirred for 2 hours to form a homogeneous casting dope. The resulting homogeneous casting dope was filtered and allowed to degas overnight. The NPI-1 polymer dense film membrane was prepared from the bubble free casting dope on a clean glass plate using a doctor knife with a 20-mil gap. The membrane together with the glass plate was then put into a vacuum oven. The solvents were removed by slowly increasing the vacuum and the temperature of the vacuum oven. Finally, the membrane was dried at 200° C. under vacuum for at least 48 hours to completely remove the residual solvents to form a polymer membrane in dense film.

Example 2

Evaluation of the $CO_2/CH_4$ and $H_2/CH_4$ Separation Performance of NPI-1 Membrane Prepared in Example 1

The NPI-1 membrane in dense film form was tested for $CO_2/CH_4$ and $H_2/CH_4$ separations at 50° C. under 791 kPa (100 psig) pure gas feed pressure. The results show that the new NPI-1 membrane has intrinsic $CO_2$ permeability of 73.4 Barrers (1 Barrer=$10^{-10}$ $cm^3$ (STP) $cm/cm^2$ s (cm Hg)) and single-gas $CO_2/CH_4$ selectivity of 25.3 at 50° C. under 791 kPa for $CO_2/CH_4$ separation. This membrane also has intrinsic $H_2$ permeability of 136.6 Barrers and single-gas $H_2/CH_4$ selectivity of 47.1 at 50° C. under 791 kPa for $H_2/CH_4$ separation.

Example 3

Preparation of NPI-1 Polyimide Hollow Fiber Membrane Using NPI-1 Polyimide Prepared in Example 1

A hollow fiber spinning dope containing 29.7 g of NPI-1 polyimide from Example 1, 62.86 g of NMP, 8.48 g of 1,3-dioxolane, 2.51 g of isopropanol, and 2.51 g of acetone was prepared. The spinning dope was extruded at a flow rate of 2.6 mL/min through a spinneret at 50° C. spinning temperature. A bore fluid containing 10% by weight of water in NMP was injected to the bore of the fiber at a flow rate of 0.8 mL/min simultaneously with the extruding of the spinning dope. The nascent fiber traveled through an air gap length of 5 cm at room temperature with a humidity of 25%, and then was immersed into a water coagulant bath at 21° C. and wound up at a rate of 8.0 m/min. The water-wet fiber was annealed in a hot water bath at 85° C. for 30 minutes. The annealed water-wet fiber was then sequentially exchanged with methanol and hexane for three times and for 30 minutes each time, followed by drying at 100° C. in an oven for 1 hour to form NPI-1 hollow fiber membrane.

Example 4

Synthesis of poly(3,3',4,4'-diphenylsulfone tetracarboxylic dianhydride-3,3',4,4'-biphenyl tetracarboxylic dianhydride-2,4,6-trimethyl-m-phenylenediamine-3,3',5,5'-tetramethyl-4,4'-methylene dianiline) (Referred to as NPI-2)

An aromatic polyimide, poly(3,3',4,4'-diphenylsulfone tetracarboxylic dianhydride-3,3',4,4'-biphenyl tetracarboxylic dianhydride-2,4,6-trimethyl-m-phenylenediamine-3,3',5,5'-tetramethyl-4,4'-methylene dianiline) (referred to as NPI-2) containing UV cross-linkable sulfonic groups, was synthesized by polycondensation reaction of DSDA and 3,3',4,4'-biphenyl tetracarboxylic dianhydride (BPDA) with 3,3',5,5'-tetramethyl-4,4'-methylene dianiline (TMMDA) and TMPDA (DSDA:BPDA:TMMDA:TMPDA=3.06:1.02:2.00:2.00 (molar ratio)) in DMAc polar solvent. A 500 mL three-neck round-bottom flask equipped with a nitrogen inlet and a mechanical stirrer was charged with 17.8 g of TMMDA, 10.5 g of TMPDA, and 60 g of DMAc. Once TMMDA and TMPDA were fully dissolved, 38.3 g of DSDA and 10.5 g of BPDA solid powder was added to the solution of TMMDA and TMPDA stepwise under stirring in the flask. 40 g of DMAc was added to the solution after the DSDA and BPDA powder was added. Another 30 g of DMAc was added after about 10 min. The reaction mixture was then heated to 70° C. to completely dissolve the powder. Another 130 g of DMAc was added to the reaction mixture after it was heated at 70° C. for 0.5 hour. The reaction mixture was then cooled down to ambient temperature and was mechanically stirred for 24 hours at ambient temperature to give a viscous poly(amic acid) solution. Then 31.4 g of acetic anhydride was added slowly to the reaction mixture under stirring followed by the addition of 48.7 g of pyridine to the reaction mixture. The reaction mixture was mechanically stirred for an additional 2 hours at 90° C. to yield NPI-2. The polyimide NPI-2 product in a fine fiber form was recovered by slowly precipitating the reaction mixture into a large amount of methanol. The resultant polyimide NPI-2 fibers were then thoroughly rinsed with methanol and dried in a vacuum oven at 100° C. for 24 hours.

Example 5

Preparation of NPI-2 Dense Film Membrane

The NPI-2 dense film membrane was prepared as follows: 7.0 g of polyimide NPI-2 was dissolved in a solvent mixture of 15.5 g of NMP and 12.5 g of 1,3-dioxolane. The mixture was mechanically stirred for 2 hours to form a homogeneous casting dope. The resulting homogeneous casting dope was filtered and allowed to degas overnight. The NPI-2 dense film membrane was prepared from the bubble free casting dope on a clean glass plate using a doctor knife with a 20-mil gap. The dense film together with the glass plate was then put into a vacuum oven. The solvents were removed by slowly increasing the vacuum and the temperature of the vacuum oven. Finally, the dense film was dried at 200° C. under vacuum for at least 48 hours to completely remove the residual solvents to form NPI-2 dense film membrane.

Example 6

Preparation of UV Cross-Linked NPI-2 Dense Film Membrane

The NPI-2 dense film membrane prepared in Example 5 was further UV cross-linked by exposure to UV radiation using 254 nm wavelength UV light generated from a UV lamp with 1.9 cm (0.75 inch) distance from NPI-3 dense film membrane surface to the UV lamp and a radiation time of 10 min at 50° C. The UV lamp described here is a low pressure, mercury arc immersion UV quartz 12 watt lamp with 12 watt power supply from Ace Glass Incorporated.

Example 7

Synthesis of poly(3,3',4,4'-benzophenone tetracarboxylic dianhydride-pyromellitic dianhydride-2,4,6-trimethyl-m-phenylenediamine) (Referred to as NPI-3)

An aromatic polyimide, poly(3,3',4,4'-benzophenone tetracarboxylic dianhydride-pyromellitic dianhydride-2,4,6-trimethyl-m-phenylenediamine) (referred to as NPI-3) containing UV cross-linkable carbonyl groups, was synthesized by polycondensation reaction of 3,3',4,4'-benzophenone tetracarboxylic dianhydride (BTDA) and pyromellitic dianhydride (PMDA) with TMPDA (BTDA:PMDA:TMPDA=2.04:2.04:4.00 (molar ratio)) in NMP polar solvent. The synthesis procedure for NPI-3 was the same as that described in Example 4 for NPI-2 except different monomers and solvent were used for the synthesis of NPI-3.

Example 8

Preparation of NPI-3 Dense Film Membrane

The NPI-3 dense film membrane was prepared using a similar procedure as described in Example 5 except the polymer used for making the dense film membrane is NPI-3.

Example 9

Preparation of UV Cross-Linked NPI-3 Dense Film Membrane

The NPI-3 dense film membrane prepared in Example 8 was further UV cross-linked by exposure to UV radiation using 254 nm wavelength UV light generated from a UV lamp with 1.9 cm (0.75 inch) distance from NPI-3 dense film surface to the UV lamp and a radiation time of 10 min at 50° C. The UV lamp described here is a low pressure, mercury arc immersion UV quartz 12 watt lamp with 12 watt power supply from Ace Glass Incorporated.

Example 10

$CO_2/CH_4$ and $H_2/CH_4$ Separation Properties of Dense Film Membranes

The permeabilities of $CO_2$, $H_2$, and $CH_4$ ($P_{CO2}$, $P_{H2}$, and $P_{CH4}$) and selectivity of $CO_2/CH_4$ ($\alpha_{CO2/CH4}$) and $H_2/CH_4$ ($\alpha_{H2/CH4}$) of the dense film membranes prepared in Examples 5, 6, 8 and 9, respectively, were measured by pure gas measurements at 50° C. under about 790 kPa (100 psig) pressure. The results are shown in Table 1.

TABLE 1

Pure gas permeation test results of dense film membranes for $CO_2/CH_4$ and $H_2/CH_4$ separations [a]

| Dense film | $P_{CO2}$ (Barrer) | $\alpha_{CO2/CH4}$ | $P_{H2}$ (Barrer) | $\alpha_{H2/CH4}$ |
|---|---|---|---|---|
| NPI-2 | 57.5 | 20.2 | 109.9 | 38.6 |
| NPI-2-UV treated | 22.5 | 38.8 | 99.0 | 171 |
| NPI-3 | 179.0 | 15.8 | 256.5 | 22.7 |
| NPI-3-UV treated | 64.1 | 39.8 | 224.1 | 139.2 |

[a] Tested at 50° C. under 790 kPa (100 psig) pure gas pressure;
1 Barrer = $10^{-10}$ (cm$^3$(STP)·cm)/(cm$^2$·sec·cmHg)

Example 11

Preparation of NPI-2 Hollow Fiber Membranes

A polymer dope consisting of 52.1 g n-methylpyrrolidinone (NMP), 7.0 g 1,3-dioxolane, 2.1 g 2-propanol, 2.1 g acetone, and 23.4 g of NPI-2 polyimide synthesized in Example 4 was mixed until uniform. The viscosity of this dope was approximately 280,000 cP at 30° C. This dope was extruded from the annulus of a hollow fiber membrane spinneret at a flow rate ranging from 0.7 to 3.0 mL/min. At the same time, a bore solution of 10 wt % $H_2O$/90 wt % NMP flowed from the inner passage of the spinneret at 0.4 to 0.8 mL/min to keep the nascent fiber from collapsing on itself. During extrusion, the dope and spinneret were controlled at 50° C. The nascent fiber passed through an air gap of 3 to 10 cm and then entered a water coagulation bath at approximately 4° C. to allow liquid-liquid demixing and formation of the asymmetric porous portion of the hollow fiber membrane. Finally, the solidified hollow fiber membrane was wound on a take-up drum partially submersed in room temperature water at 8 to 37 m/min. The resulting NPI-2 hollow fiber membranes had a dense selective layer on the outside surface of the fibers.

The newly formed hollow fibers were treated in 85° C. water for 30 min then soaked in a water bath at room temperature overnight. Then, the fibers were submersed in three successive volumes of methanol for 30 min each, followed by submersion in three successive volumes of hexane for 30 min each. These steps were done to remove residual solvents from the fibers. Next, the fibers were dried for 1 hour at 100° C., and then bundles of fibers were sealed into modules for gas permeation testing. Details of the specific conditions used for each NPI-2 hollow fiber membrane are shown in Table 2.

Example 12

Preparation of NPI-3 Hollow Fiber Membranes

A polymer dope consisting of 62.6 g NMP, 8.5 g 1,3-dioxolane, 2.5 g 2-propanol, 2.5 g acetone, and 24.0 g of NPI-3 polyimide synthesized in Example 7 was mixed until uniform. The viscosity of this dope was approximately 300,000 cP at 30° C. This dope was extruded from the annulus of a hollow fiber membrane spinneret at a flow rate ranging from 0.7 to 3.0 mL/min. At the same time, a bore solution of 10 wt % $H_2O$/90 wt % NMP flowed from the inner passage of the spinneret at 0.4 to 0.8 mL/min to keep the nascent fiber from collapsing on itself. During extrusion, the dope and spinneret were controlled at 50° C. The nascent fiber passed through an air gap of 3 to 10 cm and then entered a water coagulation bath at approximately 3° C. Finally, the solidified hollow fiber membrane was wound on a take-up drum partially submersed in room temperature water at 8 to 30 m/min. The resulting membranes had a dense selective layer on the outside surface of the fibers. Details of the specific conditions used for each of the hollow fiber NPI-3 membranes are shown in Table 3.

A second polymer dope consisting of 70.5 g NMP, 3.5 g 2-propanol, 1.2 g lactic acid, and 22.5 g of NPI-3 synthesized in Example 7 was mixed until uniform. The viscosity of this dope was approximately 210,000 cP at 30° C. This dope was extruded from the annulus of a hollow fiber membrane spinneret at a flow rate ranging from 0.7 to 3.0 mL/min. At the same time, a bore solution of 10 wt % $H_2O$/90 wt % NMP flowed from the inner passage of the spinneret at 0.4 to 0.8 mL/min to keep the nascent fiber from collapsing on itself. During extrusion, the dope and spinneret were controlled at 50° C. The nascent fiber passed through an air gap of 3 to 10 cm and then entered a water coagulation bath at approximately 5° C. Finally, the solidified hollow fiber membrane was wound on a take-up drum partially submersed in room temperature water at 8 to 37 m/min. The resulting NPI-3 hollow fiber membranes had a dense selective layer on the outside surface of the fibers. Details of the specific conditions used for each of the hollow fiber membranes are shown in Table 4.

The newly formed hollow fibers from each set of membranes were treated in 85° C. water for 30 min then soaked in a water bath at room temperature overnight. Then, the fibers were submersed in three successive volumes of methanol for 30 min each, followed by submersion in three successive volumes of hexane for 30 min each. Next, the fibers were dried for 1 hour at 100° C., and then bundles of fibers were sealed into modules for gas permeation testing.

Example 13

$CO_2/CH_4$ Separation Properties of NPI-2 Polyimide Hollow Fiber Membranes

The polyimide hollow fiber membranes prepared from NPI-2 polyimide in Example 11 were tested for single-gas permeation of $CO_2$ and $CH_4$ at 50° C. with the feed at 790 kPa (100 psig) and the permeate at approximately 101 kPa (0 psig). Performance of these membranes is shown in Table 2 along with the unique fabrication conditions for each membrane. Other fabrication conditions for these membranes were described in Example 11. All of the NPI-2 polyimide hollow fiber membranes shown in Table 2 were nearly defect-free and had $CO_2/CH_4$ selectivities near to or higher than the intrinsic selectivity of the NPI-2 dense film membrane.

TABLE 2

Single-gas $CO_2/CH_4$ permeation performance of NPI-2 hollow fiber membranes.

| Membrane # | Air gap (cm) | Dope rate (mL/min) | Bore rate (mL/min) | Take-up rate (m/min) | Single gas $P_{CO_2}/L$ (A.U.) | $\alpha_{CO2/CH4}$ |
|---|---|---|---|---|---|---|
| 1 | 10 | 0.7 | 0.4 | 8.0 | 21.2 | 38.6 |
| 2 | 5 | 0.7 | 0.4 | 8.0 | 16.6 | 22.8 |
| 3 | 10 | 2.6 | 0.8 | 23.5 | 33.5 | 27.9 |
| 4 | 7 | 2.6 | 0.8 | 23.5 | 31.8 | 25.7 |
| 5 | 3 | 2.6 | 0.8 | 23.5 | 30.2 | 15.3 |
| 6 | 10 | 3.0 | 0.6 | 23.5 | 22.5 | 34.4 |
| 7 | 7 | 3.0 | 0.6 | 23.5 | 22.3 | 23.8 |
| 8 | 7 | 3.0 | 0.6 | 30.2 | 24.0 | 26.9 |
| 9 | 7 | 3.0 | 0.6 | 36.9 | 26.2 | 26.4 |
| 10 | 3 | 3.0 | 0.6 | 23.5 | 33.9 | 20.9 |
| 11 | 3 | 3.0 | 0.6 | 23.5 | 33.9 | 20.9 |

(1 A.U. = 1 ft³ (STP)/h · ft² · 100 psi)

Example 14

$CO_2/CH_4$ Separation Properties of NPI-3 Hollow Fiber Membranes

The polyimide hollow fiber membranes prepared from NPI-3 in Example 12 were tested for single-gas permeation of $CO_2$ and $CH_4$ at 50° C. with the feed at 790 kPa (100 psig) and the permeate at approximately 101 kPa (0 psig). Two different sets of NPI-3 hollow fiber membranes were prepared using different dope formulations, as described in Example 12. Performance of these membranes is shown in Tables 3 and 4 along with the unique fabrication conditions for each membrane. Other fabrication conditions for these membranes were described in Example 12. All of the polyimide NPI-3 hollow fiber membranes shown in Tables 3 and 4 were nearly defect-free and had $CO_2/CH_4$ selectivities higher than the intrinsic selectivity of the NPI-2 hollow fiber membranes.

TABLE 3

Single-gas $CO_2/CH_4$ permeation performance of NPI-3 hollow fiber membranes prepared using a dope consisting of 62.6 g NMP, 8.5 g 1,3-dioxolane, 2.5 g 2-propanol, 2.5 g acetone, and 24.0 g of NPI-3 polyimide.

| Membrane # | Air gap (cm) | Dope rate (mL/min) | Bore rate (mL/min) | Take-up rate (m/min) | Single gas $P_{CO_2}/L$ (A.U.) | $\alpha_{CO2/CH4}$ |
|---|---|---|---|---|---|---|
| 12 | 10 | 0.7 | 0.4 | 8.0 | 8.8 | 35.8 |
| 13 | 10 | 2.6 | 0.8 | 23.5 | 15.5 | 29.7 |
| 14 | 7 | 2.6 | 0.8 | 23.5 | 15.8 | 21.6 |
| 15 | 3 | 2.6 | 0.8 | 23.5 | 20.5 | 30.5 |
| 16 | 7 | 3.0 | 0.6 | 23.5 | 16.4 | 27.2 |
| 17 | 7 | 3.0 | 0.6 | 30.2 | 19.8 | 21.4 |
| 18 | 3 | 3.0 | 0.6 | 23.5 | 17.2 | 20.7 |

(1 A.U. = 1 ft³ (STP)/h · ft² · 100 psi)

TABLE 4

Single-gas $CO_2/CH_4$ permeation performance of NPI-3 hollow fiber membranes prepared using a dope consisting of 70.5 g NMP, 3.5 g 2-propanol, 1.2 g lactic acid, and 22.5 g of NPI-3.

| Membrane # | Air gap (cm) | Dope rate (mL/min) | Bore rate (mL/min) | Take-up rate (m/min) | Single gas $P_{CO_2}/L$ (A.U.) | $\alpha_{CO2/CH4}$ |
|---|---|---|---|---|---|---|
| 19 | 10 | 0.7 | 0.4 | 8.0 | 17.3 | 25.1 |
| 20 | 10 | 2.6 | 0.8 | 23.5 | 21.3 | 26.1 |
| 21 | 7 | 2.6 | 0.8 | 23.5 | 20.4 | 25.1 |
| 22 | 10 | 3.0 | 0.6 | 23.5 | 23.3 | 21.3 |
| 23 | 7 | 3.0 | 0.6 | 23.5 | 20.9 | 22.7 |
| 24 | 7 | 3.0 | 0.6 | 30.2 | 17.3 | 30.0 |
| 25 | 3 | 3.0 | 0.6 | 23.5 | 23.5 | 23.6 |

(1 A.U. = 1 ft³ (STP)/h · ft² · 100 psi)

Example 15

Preparation of Blend Dense Film Membrane of NPI-2/PES

A blend polymer dense film membrane of NPI-2 polyimide and polyethersulfone (PES) was prepared as follows: 3.5 g of polyimide NPI-2 and 3.5 g of PES were dissolved in a solvent mixture of 15.5 g of NMP and 12.5 g of 1,3-dioxolane. The mixture was mechanically stirred for 2 hours to form a homogeneous casting dope. The resulting homogeneous casting dope was filtered and allowed to degas overnight. The NPI-2/PES blend dense film membrane was prepared from the bubble free casting dope on a clean glass plate using a doctor knife with a 20-mil gap. The dense film together with the glass plate was then put into a vacuum oven. The solvents were removed by slowly increasing the vacuum and the temperature of the vacuum oven. Finally, the dense film was dried at 200° C. under vacuum for at least 48 hours to completely remove the residual solvents to form NPI-2/PES blend dense film membrane.

The invention claimed is:

1. A process for separating at least one gas from a mixture of gases, the process comprising:
   a) providing a polyimide gas separation membrane comprising an aromatic polyimide polymer that comprises a plurality of first repeating units of formula (I)

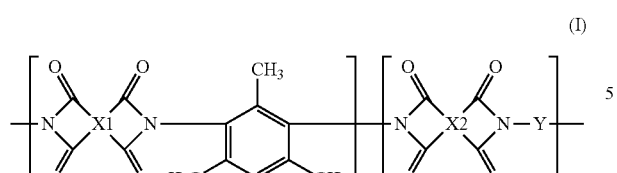

wherein X1 is

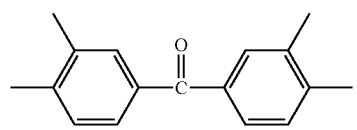

X2 is selected from the group consisting of

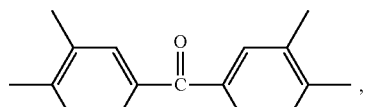

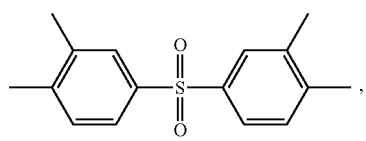

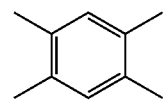

and mixtures thereof, wherein Y is selected from the group consisting of

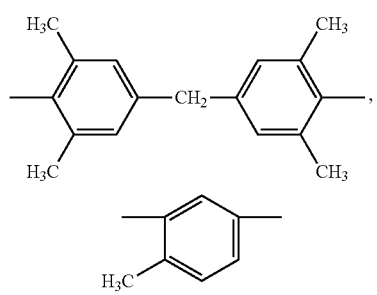

and mixtures thereof and wherein n and m are independent integers from 2 to 500;
  b) contacting the mixture to one side of said polyimide gas separation membrane to cause said at least one gas to permeate the said polyimide gas separation membrane; and
  c) removing from an opposite side of the said polyimide gas separation membrane a permeate gas composition comprising a portion of said at least one gas which permeated said membrane.

2. The process of claim 1 wherein X2 is

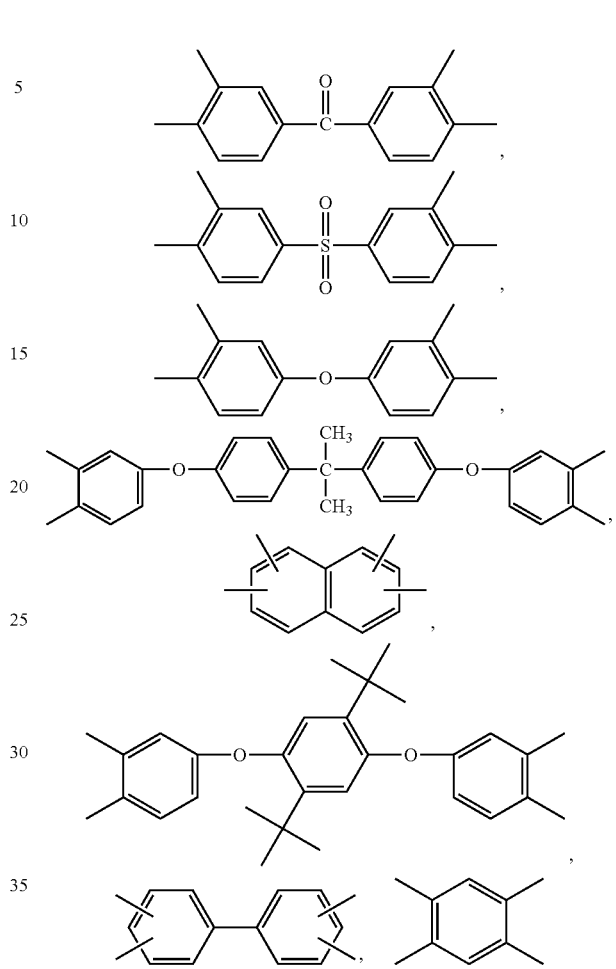

wherein Y is

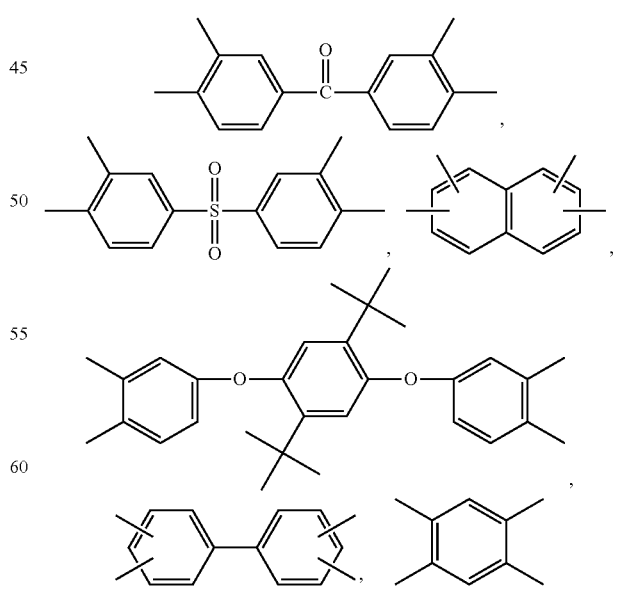

and wherein n and m are independent integers from 2 to 500.

3. The process of claim 1 wherein X2 is
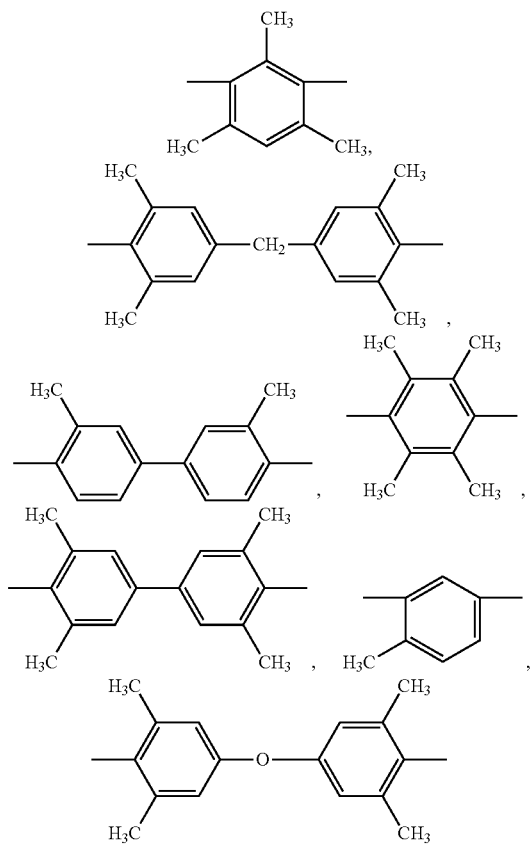
wherein Y is
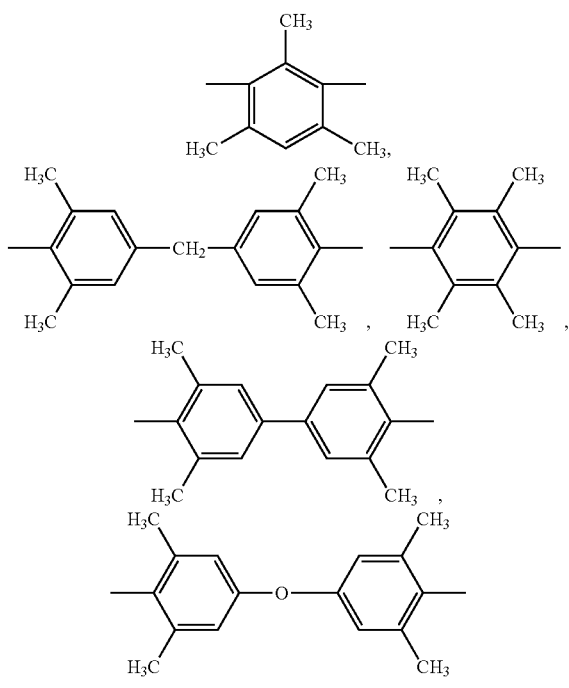
and wherein n and m are independent integers from 2 to 500.
4. The process of claim 1 wherein X2 is a mixture of
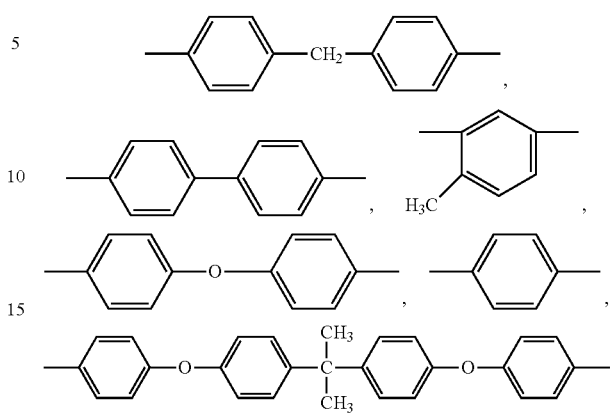
wherein Y is
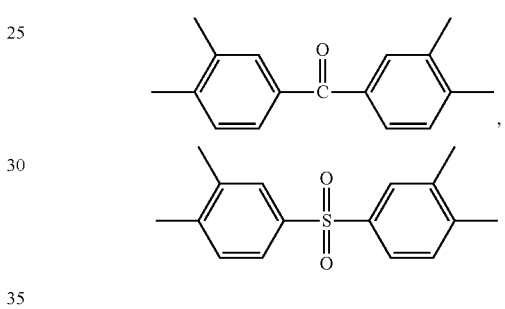
and wherein n and m are independent integers from 2 to 500.
5. The process of claim 1 wherein X2 is a mixture of
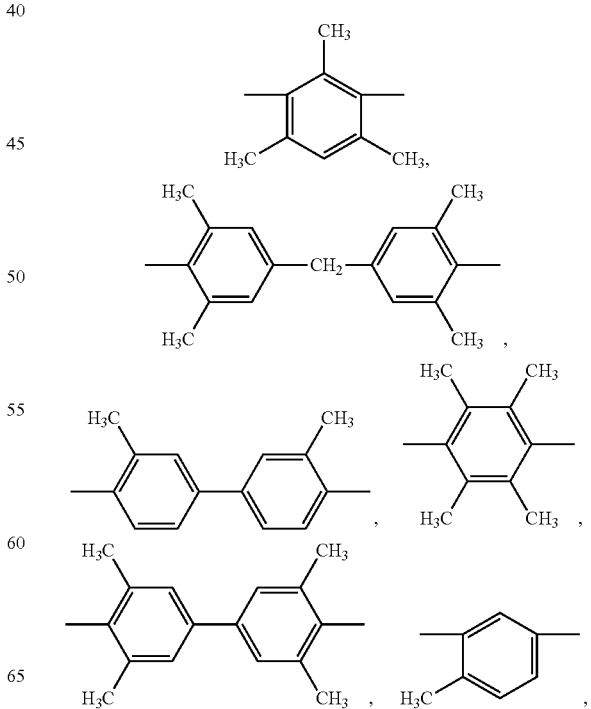

-continued
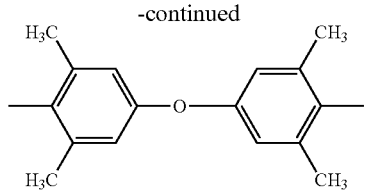
wherein Y is
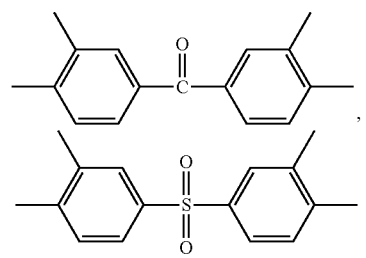
and wherein n and m are independent integers from 2 to 500.
6. The process of claim 1 wherein said mixture of gases comprises a mixture of at least one gas selected from carbon dioxide and hydrogen sulfide that is mixed with methane.
* * * * *